(12) United States Patent
Wittwer et al.

(10) Patent No.: US 6,197,520 B1
(45) Date of Patent: Mar. 6, 2001

(54) SOLUTION-BASED COLOR COMPENSATION ADJUSTED FOR TEMPERATURE AND ELECTRONIC GAINS

(75) Inventors: Carl T. Wittwer; Gregory Pritham; Philip Bernard, all of Salt Lake City, UT (US)

(73) Assignee: University of Utah Research Foundation, Salt Lake City, UT (US)

( * ) Notice: Subject to any disclaimer, the term of this patent is extended or adjusted under 35 U.S.C. 154(b) by 0 days.

(21) Appl. No.: 09/374,422

(22) Filed: Aug. 13, 1999

(51) Int. Cl.$^7$ ............................... C12Q 1/68; C12P 19/34
(52) U.S. Cl. ............................. 435/6; 435/91.2; 436/94
(58) Field of Search ..................... 435/6, 91.2; 436/94

(56) References Cited

U.S. PATENT DOCUMENTS

| | | | |
|---|---|---|---|
| 4,704,891 | * 11/1987 | Recktenwald et al. | 73/1 R |
| 4,857,451 | * 8/1989 | Schwartz | 435/7 |
| 4,876,190 | * 10/1989 | Recktenwald | 435/7 |
| 5,093,234 | * 3/1992 | Schwartz | 435/7.21 |
| 5,455,175 | 10/1995 | Wittwer et al. | 435/286.1 |
| 5,675,517 | * 10/1997 | Stokdijk | 364/571.01 |
| 5,830,679 | * 11/1998 | Bianchi et al. | 435/7.24 |

OTHER PUBLICATIONS

Bernard et al., Analyt. Biochem. 273, 221–228, 1999.*
Bagwell C.B. and Adams, E.g. Fluorescence Spectral Overlap Compensation For Any Number Of Flow Cytometry Parameters. Ann. NY Acad. Sci., 677:167–184 (1993).
Bernard, P.S., et al. Integrated Amplification and Detection of the C677T Point Mutation in the Methylenetetrahydrofolate Reductase Gene by Fluorescence Resonance Energy Transfer and Probe Melting Curves. Anal. Biochem. 255, 101–107 (1998).
Egholm. M., et al. PNA hybridizes to complementary oligonucleotides obeying the Watson–Crick hydrogen–bonding rules. Nature 365, 566–568 (1993).
Lay, M.J. and Wittwer, C.T. Real–time fluorescence genotyping of factor V Leiden during rapid–cycle PCR. Clin. Chem. 43, 2262–2267 (1997).
Loken, M.R., et al., Two–Color Immunofluorescence Using A fluorescence–Activated Cell Sorter. J. Histochem. and Cytochem., 25:899–907 (1977).
Mansfield, E.S., et al. Rapid sizing of polymorphic microsatellite markers by capillary array electrophoresis. J. Chromatogr. A, 781, 295–305 (1997).
Mahley, R.W. Apolipoprotein E: Cholesterol Transport Protein with Expanding Role in Cell Biology. Science 240, 622–630 (1988).
Pastinen, T., et al. Multiplex, fluorescent, solid–phase minisequencing for efficient screening of DNA sequence variation. Clin. Chem. 42, 1391–1397 (1996).
Samiotaki, M., et al. Seven–Color Time–Resolved Fluroescenc Hybridization Analysis of Human Papilloma Virus Types. Anal. Biochem. 253, 156–161 (1997).
Shapiro, H.M. Compensating without decompensating, in Practical Flow Cytometry, 3$^{rd}$ edition, Wiley–Liss, Inc., New York, NY. 214–215 (1995).
Sidhu, M.K., et al. Quantitative Detection of Mycoplasma DNA Using Competetive PCR, in Gene Quantification,. Birkhauser, Boston, MA., Ferre, F., Ed. 265–276 (1998).
Wetmur, J.G. Nucleic Acid Hybrids, Formation and Structure of, in Molecular Biology and Biotechnology. Meyers, R.A., ed. VCH Publishers, Inc., New York, NY. 605–608 (1995).
Wittwer, C.T., et al. Continuous Fluorescence Monitoring of Rapid Cycle DNA Amplification. BioTechniques 22, 130–138 (1997).

* cited by examiner

*Primary Examiner*—Kenneth R. Horlick
(74) *Attorney, Agent, or Firm*—Barnes & Thornburg

(57) ABSTRACT

The present invention is directed to a method of analyzing at least two analytes at the same time using at least two fluorescent detecting entities. More particularly, the present invention relates to the use of fluorescently labeled hybridization probes to identify the genotypes of a nucleic acid sample at more than one locus by measuring fluorescence throughout a range of temperatures and correcting for temperature-dependent spectral overlap of the fluorescent probes.

18 Claims, 8 Drawing Sheets

1mM Mg

3mM Mg

SEQUENCE LISTING

<160> NUMBER OF SEQ ID NOS: 8

<210> SEQ ID NO 1
<211> LENGTH: 56
<212> TYPE: DNA
<213> ORGANISM: Homo sapiens

<400> SEQUENCE: 1
ggcgcaggcc cggctgggcg cggacatgga ggacgtgtgc ggccgcctgg tgcagt        56

<210> SEQ ID NO 2
<211> LENGTH: 56
<212> TYPE: DNA
<213> ORGANISM: Homo sapiens

<400> SEQUENCE: 2
ggcgcaggcc cggctgggcg cggacatgga ggacgtgcgc ggccgcctgg tgcagt        56

<210> SEQ ID NO 3
<211> LENGTH: 17
<212> TYPE: DNA
<213> ORGANISM: Homo sapiens

<400> SEQUENCE: 3
ccaggcggcc gcacacg                                                   17

<210> SEQ ID NO 4
<211> LENGTH: 30
<212> TYPE: DNA
<213> ORGANISM: Homo sapiens

<400> SEQUENCE: 4
cctccatgtc cgcgcccagc cgggcctgcg                                     30

<210> SEQ ID NO 5
<211> LENGTH: 51
<212> TYPE: DNA
<213> ORGANISM: Homo sapiens

<400> SEQUENCE: 5
gcggctcctg cccgatgccg atgacctgca gaagtgcctg gcagtgtacc a             51

<210> SEQ ID NO 6
<211> LENGTH: 51
<212> TYPE: DNA
<213> ORGANISM: Homo sapiens

<400> SEQUENCE: 6
gcggctcctg cccgatgccg atgacctgca gaagcgcctg gcagtgtacc a             51

<210> SEQ ID NO 7
<211> LENGTH: 17
<212> TYPE: DNA
<213> ORGANISM: Homo sapiens

<400> SEQUENCE: 7

-continued

```
acactgccag gcacttc                                              17

<210> SEQ ID NO 8
<211> LENGTH: 29
<212> TYPE: DNA
<213> ORGANISM: Homo sapiens

<400> SEQUENCE: 8
gccaggtcat cggcatcggg gcaggagcc                                 29
```

SOLUTION-BASED COLOR COMPENSATION ADJUSTED FOR TEMPERATURE AND ELECTRONIC GAINS

FIELD OF THE INVENTION

The present invention is directed to a method of analyzing at least two analytes at the same time using at least two fluorescent detecting entities. More particularly, the present invention relates to the use of fluorescently labeled hybridization probes to identify the genotypes at more than one nucleic acid locus by correcting for temperature-dependent spectral overlap of the fluorescent probes.

BACKGROUND AND SUMMARY OF THE INVENTION

The continued discovery of novel genes provides a resource of genetic material for studying the association between genotype and disease. See Kononen, J., et al. (1998) Nat. Med. 4, 844–847. The majority of genetic diseases are due to single base alterations that may be found at multiple sites within one or several genes. See Cooper, D. N., and Krawczak, M. (1990) Hum. Genet. 85, 55–74; Neufeld, E. J. (1998) Hematol. Oncol. Clin. North Am. 12, 1193–1209. For this reason, techniques for nucleic acid analysis often require analysis of multiple loci and sequence variants. For convenience, it is preferable to perform this analysis in a single reaction.

Different colored fluorescent dyes are frequently used to increase the quantity of information obtained from a nucleic acid sample. Mansfield, E. S., et al. (1997) J. Chromatogr. A. 781, 295–305; Samiotaki, M., et al. (1997) Anal. Biochem. 253, 156–161. These dyes can be attached to primers or probes and the products analyzed either during PCR amplification or by post-amplification detection methods. Pritham, G. H., and Wittwer, C. T. (1998) J. Clin. Lig. Assay. 21, 1–9. Although post-amplification analysis increases assay time, post-amplification analysis provides a second level of investigation that multiplies the power of the assay. For example, multicolor fluorescence detection in combination with product sizing has been successful for identity typing using short tandem repeats, genotyping single base changes by minisequencing, genotyping by competitive priming. Mansfield, E. S., et al. (1997) J. Chromatogr. A. 781, 295–305; Pritham, G. H., and Wittwer, C. T. (1998) J. Clin. Lig. Assay. 21, 1–9; Pastinen, T., et al. (1996) Clin. Chem. 42, 1391–1397.

Hybridization probes provide an elegant system for homogenous PCR amplification and genotyping. See Lay, M. J., and Wittwer, C. T. (1997) Clin. Chem. 43, 2262–2267; Bernard, P. S., et al. (1998) Anal. Biochem. 255, 101–107; Bernard, P. S., et al. (1998) Am. J. Pathol. 153, 1055–1061. In one such system, two oligonucleotide probes that hybridize to adjacent regions of a DNA sequence are employed, wherein each oligonucleotide probe is labeled with a respective member of a fluorescent energy transfer pair. In this system, a donor fluorescent dye is excited and transfers energy to an acceptor fluorescent dye if the two dyes are in close proximity, as they would be when hybridized to adjacent regions of the DNA sequence. Post-amplification melting curve analysis allows at least two alleles to be identified using this single pair hybridization probes. This is because variations in DNA sequences create mismatches with the probe resulting in characteristic $T_m$ shifts that are measured by monitoring changes in fluorescence resonance energy transfer during slow heating.

Probes having different $T_m$s with a variety of alleles can be multiplexed together to increase the power of this technique (Bernard, P. S., et al. (1998) Am. J. Pathol. 153, 1055–1061); however, multiplexing is ultimately limited by the number of $T_m$s that can be differentiated over a range of probe melting temperatures. The present invention is directed to expanding the power of hybridization probe multiplexing by using color as well as $T_m$ for genotyping different alleles at one time. Multiple probes having different acceptor dyes are employed. Because the acceptor dyes emit at different wavelengths, such multicolor analysis can be used to expand the number of alleles which can be studied at one time.

While multicolor analysis can be used to expand the amount of information obtained in a single melting curve, multicolor analysis requires the use of crosstalk compensation techniques to correct for fluorescence overlap between channels. These methods were originally developed for multiparameter fluorescent monitoring of cells using flow cytometry. Bagwell, C. B., and Adams, E. G. (1993) Ann. N.Y. Acad. Sci. 677, 167–184. While these techniques have proven to be useful, the temperature remains constant in flow cytometry and these methods do not correct for changes in temperature-dependent crossover effects. With melting curve analysis, the temperature ranges from 40 to 95° C., and significant errors can arise if temperature-dependent crossover effects are not corrected. In order to adapt multicolor analysis for use with hybridization probes, algorithm allowances for different gain settings and for temperature effects on fluorescence overlap between channels are necessary.

The present approach is to perform a calibration run during a temperature ramp to define the temperature dependence of each fluorophore. This temperature dependence is then approximated with third degree polynomials. Then, for fluorescent value acquisition during subsequent test runs, the temperature of the acquisition is used to interpolate fluorescence calibration coefficients at that temperature. Without this correction, fluorescent values would be incorrect due to temperature dependent spectral overlap.

Furthermore, correction for amplifier gain is also desired, since experimental runs may be acquired at various gains. Because it is not practical to perform calibration runs for all gain combinations, the compensation file should work with experimental runs obtained at any gain setting. Correction for gain can be achieved by multiplying the fluorescent calibration curves by the ratio of the run gain to the calibration gain for each channel.

Thus, one aspect of this invention is directed toward a method for determining the presence of at least two analytes using at least two fluorescent detecting entities specific for their respective analytes. The fluorescent entities are excited with light having the appropriate wavelength, the fluorescence is determined in at least two spectral channels, and the fluorescent values are corrected for spectral overlap and for temperature dependence of the fluorescent values.

In another embodiment of this invention, the analytes are nucleic acid loci, and the fluorescent entities are specific for their respective loci. The fluorescent entities are excited with light having the appropriate wavelength, fluorescence is measured throughout a range of temperatures, and the signal values are compensated for temperature dependence. In a preferred embodiment, the fluorescent entities are fixed to oligonucleotides having sequences complementary to their respective loci, the oligonucleotides are annealed to the loci, and the measuring step includes monitoring the fluorescence during heating to melt the oligonucleotides from their respective loci.

The apolipoprotein ("Apo E") gene serves as a model system for the present invention. Single base alterations within codons 112 and 158 of the Apo E gene account for the three common alleles ($\epsilon2$, $\epsilon3$, and $\epsilon4$) and six phenotypes of Apo E. Mahley, R. W. (1988) Science 240,622–630. Oligonucleotide targets were synthesized to provide for adjacent hybridization probe genotyping of Apo E alleles. By using artificial templates, the effects of target concentration, complementary strand competition, probe concentration, $Mg^{++}$ concentration, and annealing conditions prior to melting curve analysis could be systematically studied irrespective of amplification technique. Thus, an additional embodiment of this invention includes optimizing target concentration and annealing conditions, and reducing complementary strand competition to provide optimal compensated fluorescent measurements.

Additional features of the present invention will become apparent to those skilled in the art upon consideration of the following detailed description of preferred embodiments exemplifying the best mode of carrying out the invention as presently perceived.

BRIEF DESCRIPTION OF THE DRAWINGS

FIG. 1A shows the equilibrium between annealing and melting at the $T_m$ of matched and unmatched duplexes; FIG. 1B is a plot of time vs temperature during the melting phase of the reaction; FIG. 1C is a plot of fluorescence vs temperature for the LC Red 640 probe; and FIG. 1D is a plot of the negative derivative of the fluorescence of FIG. 1C vs time.

FIG. 2A illustrates a rapid cooling protocol (20° C./s) down to a temperature 8° C. below the $T_m$ of a mismatched duplex; FIG. 2B illustrates the rapid cooling protocol interrupted by 20 second holds at temperatures 8° C. below the $T_m$ for the matched and then the mismatched duplex; and FIG. 2C illustrates a slower temperature transition rate (1° C./s) down to a temperature 8° C. below the $T_m$ of a mismatched duplex; FIGS. 2D–F are graphs of the negative derivative (–dF/dT) melting curves (0.1° C./s) for the annealing protocols of FIGS. 2A–C respectively.

FIG. 3A is a –dF/dT graph measuring LC Red 705 (codon 112) at 1 mM $MgCl_2$; FIG. 3B shows LC Red 705 (codon 112) at 3mM $MgCl_2$; FIG. 3C shows LC Red 640 (codon 158) at 1 mM $MgCl_2$; and FIG. 3D shows LC Red 640 (codon 158) at 3 mM $MgCl_2$. Target concentrations were at 0.05 $\mu$M (—) or 0.2 $\mu$M (- -), fluorescein probes were at 0.1 $\mu$M, the acceptor probes were at 0.2 $\mu$M, and competitor strands were not present.

FIG. 4A shows the heterozygous melting peaks for the $\epsilon3/\epsilon4$ alleles (codon 112) and FIG. 4B shows the heterozygous melting peaks for the $\epsilon2/\epsilon3$ alleles (codon 158), in the presence (—) and absence (- -) of competitor strands. Each reaction included 0.1 $\mu$M fluorescein-labeled probe, 0.2 $\mu$M acceptor probe, 0.05 $\mu$M heterozygous target with or without 0.05 $\mu$M competitor, and either 1 mM $MgCl_2$ (codon 112) or 3 mM $MgCl_2$ (codon 158).

FIG. 5A shows the original color calibration data, FIG. 5B shows the calibration data after color compensation, and FIG. 5C displays temperature correction to 50° C. after color compensation; the compensation and correction algorithms were then applied to the LC Red 705 channel in a multiplex color assay, and fluorescence vs temperature curves are shown in FIGS. 5D–F; the genotypes shown are homozygous $\epsilon4$/homozygous $\epsilon3$ ( . . . . . . ), homozygous $\epsilon3$/homozygous $\epsilon3$ (- - -), and homozygous $\epsilon3$/heterozygous $\epsilon2/\epsilon3$ (—).

FIGS. 6A–D shows multiplex color genotyping of codons 112 and 158 without competitor strand, using the annealing protocol of FIG. 2C; the uncompensated (FIG. 6A) and compensated (FIG. 6B) derivative melting curves (–dF/dT vs temperature) are shown for the LC Red 705 channel used for the analysis of codon 112; FIG. 6A shows bleed over from the LC Red 640, while FIG. 6B shows only the genotypes at codon 112; the genotypes shown are homozygous $\epsilon4$/homozygous $\epsilon3$ ( . . . . . .), homozygous $\epsilon3$/homozygous $\epsilon3$ (—), and homozygous $\epsilon3$/heterozygous $\epsilon2/\epsilon3$ (- - -).

FIG. 7A shows genotyping after cooling at 1° C./s to 42° C., the temperature used for multiplexing in FIGS. 6A–B, and FIG. 7B shows genotyping after cooling at 1° C./s to 48° C., the temperature used for genotyping optimization at codon 158.

DETAILED DESCRIPTION OF THE INVENTION

In describing and claiming the invention, the following terminology will be used in accordance with the definitions set forth below.

As used herein, "nucleic acid," "DNA," and similar terms also include nucleic acid analogs, i.e. analogs having other than a phosphodiester backbone. For example, the so-called "peptide nucleic acids," which are known in the art and have peptide bonds instead of phosphodiester bonds in the backbone, are considered within the scope of the present invention.

As used herein, "fluorescence resonance energy transfer pair" or "FRET pair" refers to a pair of fluorophores comprising a donor fluorophore and acceptor fluorophore, wherein the donor fluorophore is capable of transferring resonance energy to the acceptor fluorophore. In other words the emission spectrum of the donor fluorophore overlaps the absorption spectrum of the acceptor fluorophore. In preferred fluorescence resonance energy transfer pairs, the absorption spectrum of the donor fluorophore does not substantially overlap the absorption spectrum of the acceptor fluorophore.

As used herein, "a donor oligonucleotide probe" refers to an oligonucleotide that is labeled with a donor fluorophore of a fluorescent resonance energy transfer pair.

As used herein, "an acceptor oligonucleotide probe" refers to an oligonucleotide that is labeled with an acceptor fluorophore of a fluorescent resonance energy transfer pair.

As used herein, "FRET oligonucleotide pair" refers to the donor oligonucleotide probe and the acceptor oligonucleotide probe pair that form a fluorescence resonance energy transfer relationship when the donor oligonucleotide probe and the acceptor oligonucleotide probe are both hybridized to their complementary target nucleic acid sequences.

The present invention is directed a method for using at least two fluorescent detecting entities for determining the presence of at least two analytes. While this technique may be applied to a variety of uses, a preferred embodiment of this invention is a method of screening multiple loci of nucleic acid sequences for the presence of mutations or polymorphisms. More particularly, the present invention allows for a rapid procedure that can be entirely conducted within a single reaction vessel, for detecting mutations and polymorphisms at multiple loci of a genomic DNA sample prepared from an individual organism. While the method may be used on any suitable nucleic acid sample, the method can be performed on PCR amplification products and can be conducted within the same single reaction vessel as used for PCR amplification. The preferred method of this invention comprises the steps of combining a biological sample comprising nucleic acid sequences with two or more FRET oligonucleotide pairs, illuminating the biological sample with the appropriate wavelength, monitoring the fluorescence as a function of temperature during heating, and compensating the fluorescent values.

Figure 1A:
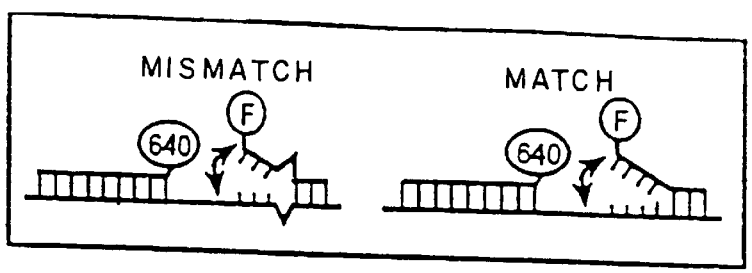
FIGS. 1A–D show a schematic display of fluorescent melting curve analysis for genotyping.
Figure 1B:
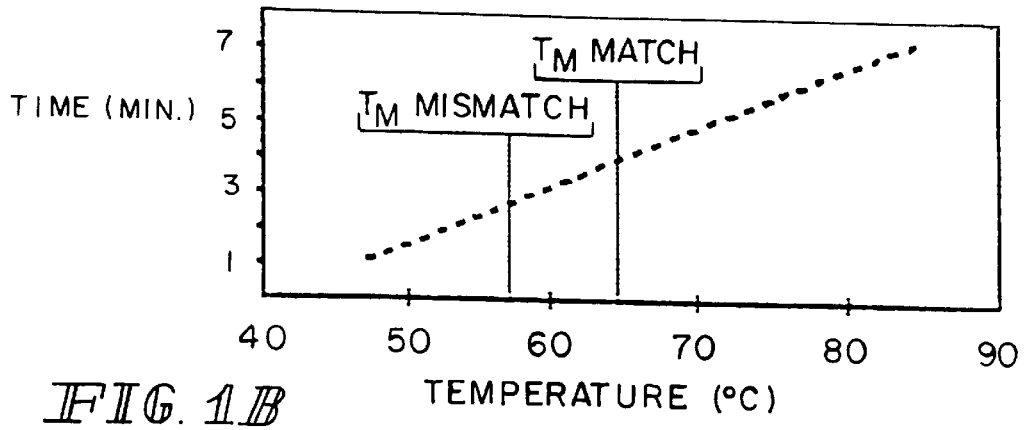
Figure 1C:
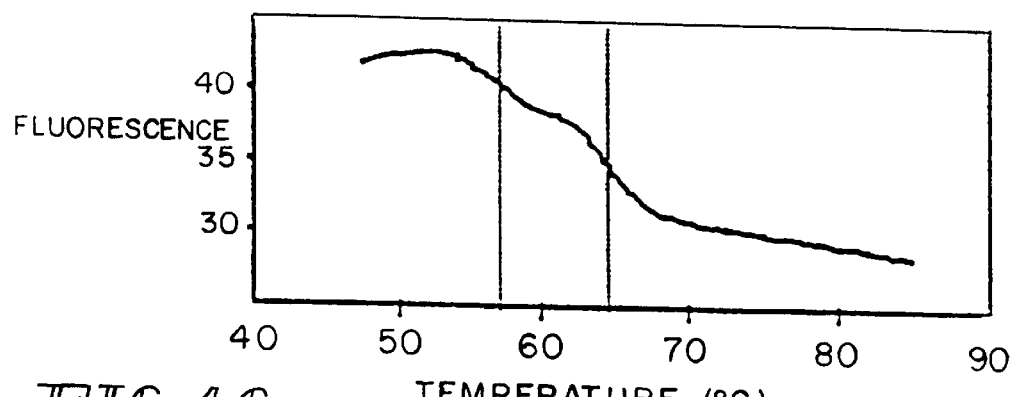
Figure 1D:
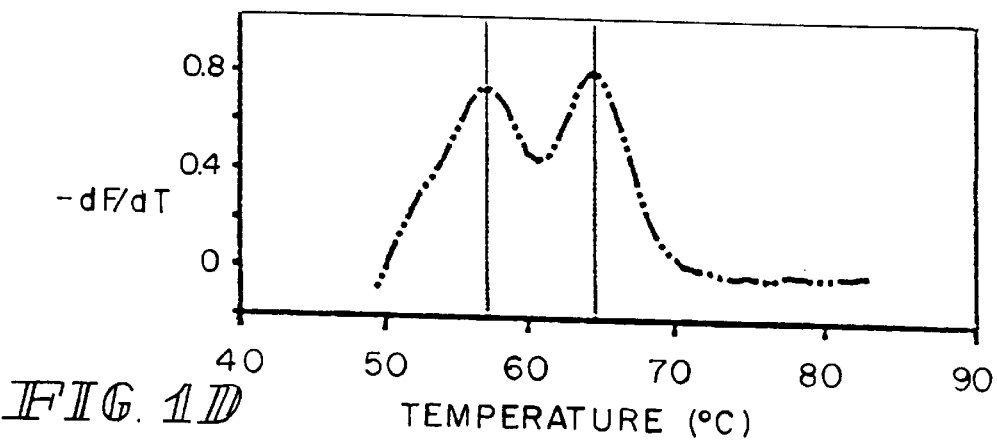

Fluorescent probes for use in detecting and monitoring DNA include double-stranded-DNA-specific dyes and sequence-specific probes. FIGS. 1A–D diagram a hybridization scheme based on resonance energy transfer between fluorophores on two adjacent probes. As further defined in Table 1, this method is sequence specific and allows analysis with melting curves. When the two labeled probes are hybridized to the same template strand, the two members of the FRET pair are brought into close proximity and energy transfer can occur (FIG. 1A). Because of a mismatch between one of the alleles and one of the oligonucleotide probes, melting will occur at a lower temperature for that allele, thus separating the members of the FRET pair. The allele containing the mismatch will have a characteristically lower $T_m$ than the allele that matches the probe (FIGS. 1B–D).

Hybridization probes specific for different alleles and labeled with different acceptor colors may be used simultaneously to multiplex fluorescent melting curves for genotyping. Two separate FRET oligonucleotide pairs, each specific for one locus and each comprising a different acceptor dye may be used at the same time. Acceptable fluorophore pairs for use as fluorescent resonance energy transfer pairs are well know to those skilled in the art and include, but are not limited to, fluorescein/rhodamine, phycoerythrin/Cy7, fluorescein/Cy5, fluorescein/Cy5.5, fluorescein/LC Red 640, and fluorescein/LC Red 705.

The nucleotide sample to be analyzed may be PCR amplification products provided using the rapid cycling techniques described in U.S. Pat. No. 5,455,175. Rapid temperature cycling is contrasted to conventional temperature cycling, wherein it is shown that 30 cycles of amplification can be completed in 15 minutes and the resulting PCR products contain many fewer side products. Thus, with rapid cycling the required times for amplification are reduced approximately 10-fold, and specificity is improved.

Real time monitoring of melting curves during slow heating can be conducted through the use of fluorescent dyes and fluorescently labeled probes. The use of real time fluorescent monitoring of nucleic acid reactions have been described in U.S. Pat. No. 5,455,175, issued on Oct. 3, 1995, and U.S. patent application Ser. Nos. 08/869,275 and 08/869,276, each filed on Jun. 4, 1997, the disclosures of which are expressly incorporated herein.

Fluorescent melting curve analysis is a rapid and effective method for genotyping. See, for example, Lay, M. J., and Wittwer, C. T. (1997) Clin. Chem. 43, 2262–2267; Bernard, P. S., et al. (1998) Anal. Biochem. 255, 101–107; Bernard, P. S., et al. (1998) Am. J. Pathol. 153, 1055–1061; Lyon, E., et al. (1998) Mol. Diag. 3, 203–210. Rapid cycle PCR and single base genotyping can be done in a single tube and without intervening steps within 40 minutes. The algorithms and methods of the present invention demonstrate that solution color multiplexing is possible with fluorescence-capable temperature cyclers such as the LightCycler™. See Wetmur J. G. (1995) in Molecular Biology and Biotechnology (Meyers, R. A., ed.), pp. 605608, VCH Publishers, Inc., New York, N.Y. This multiplexing technology could also be applied to quantification methods, such as those using internal controls for competitive PCR. Sidhu, M. K., et al. (1998) in Gene Quantification (Ferre, F., Ed.), pp. 265–276, Birkhauser, Boston, Mass.

The Apo E gene serves as a model system for the present invention. Single base alterations within codons 112 and 158 of the Apo E gene account for the three common alleles (є2, є3, and є4) and six phenotypes of Apo E. Mahley, R. W. (1988) Science 240, 622–630. Oligonucleotide targets were synthesized to provide for adjacent hybridization probe genotyping of Apo E alleles. The FRET pairs used are fluorescein/LC Red 640, and fluorescein/LC Red 705. The sequences are shown below in Table I. In addition to compensation for the temperature dependence of the fluorescent dyes, effects of target concentration, complementary strand competition, probe concentration, $Mg^{++}$ concentration, and annealing conditions prior to melting curve analysis are studied and optimized.

TABLE I

Oligonucleotides and Probes Used for Genotyping the Model Apolipoprotein E Locus Sequences for genotyping codon 112

| | | |
|---|---|---|
| є3 Target | GGCGCAGGCCCGGCTGGGCGCGGACATGGAGGA CGTGTGCGGCCGCCTGGTGCAGT [a] | [SEQ ID NO:1] |
| є4 Target | GGCGCAGGCCCGGCTGGGCGCGGACATGGAGGA CGTGCGCGGCCGCCTGGTGCAGT [a] | [SEQ ID NO:2] |
| Fluorescent probes | CCAGGCGGCCGCACACG-fluorescein | [SEQ ID NO:3] |
| | LCT705-CCTCCATGTCCGCGCCCAGCCGGGCCTGCG | [SEQ ID NO:4] |

TABLE I-continued

Oligonucleotides and Probes Used for Genotyping the Model Apolipoprotein E Locus

Sequences for genotyping codon 158

| | | | |
|---|---|---|---|
| ε2 Target | GCGGCTCCTGCCCGATGCCGATGACCTGCA<u>GAAGTGCCTGGCAGTGT</u>ACCA | [a] | [SEQ ID NO:5] |
| ε3 Target | GCGGCTCCTGCCCGATGCCGATGACCTGCA<u>GAAGCGCCTGGCAGTGT</u>ACCA | [a] | [SEQ ID NO:6] |
| Fluorescent | ACACTGCCAGGCACTTC-fluorescein | | [SEQ ID NO:7] |
| probes | LCR640-GCCAGGTCATCGGCATCGGGGCAGGAGCC | | [SEQ ID NO:8] |

[a]Underlined area indicates fluorescein probe target region; bold face indicates location of mismatch.

The rate of oligonucleotide probe/target hybridization can be determined by a single nucleation step. However, probe/target hybridization is influenced by salt concentration, temperature, and secondary structure. Wetmur, J. G. (1995) in Molecular Biology and Biotechnology (Meyers, R. A., Ed.), pp. 605–608, VCH Publishers, Inc., New York, N.Y. It is believed that these same conditions influence the quality of genotyping during probe/target melting. For instance, equivalent fluorescent melting peak areas of a heterozygous sample would require having nearly the same concentrations of probe annealed to each target prior to melting. Thus, for genotyping, annealing temperatures are selected for optimizing rates of probe/target hybridization. Empirically, maximum probe/target hybridization rates occurred 5–10° C. below the duplex $T_m$. Presently, a temperature approximately 8° C. below duplex $T_m$ is used as the target temperature.

Figure 2A:
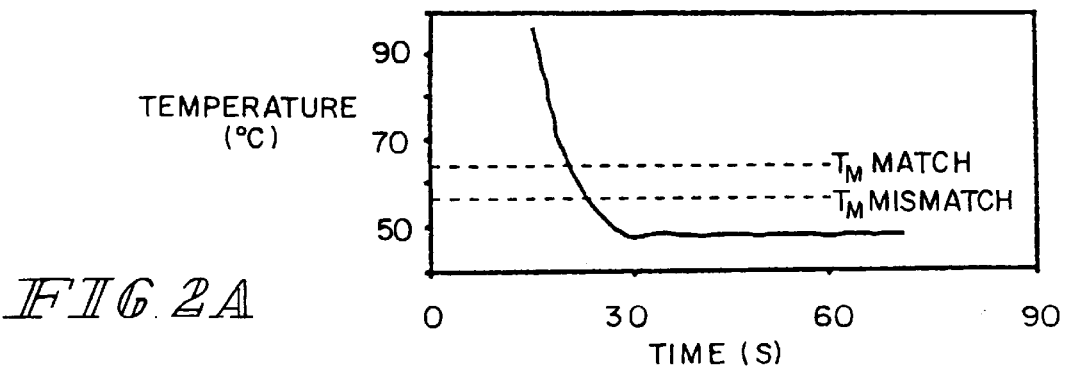
FIGS. 2A–F show the effect of different annealing protocols on the peak symmetry of derivative melting curves for a sample heterozygous at codon 158 of the Apo E gene.
Figure 2B:
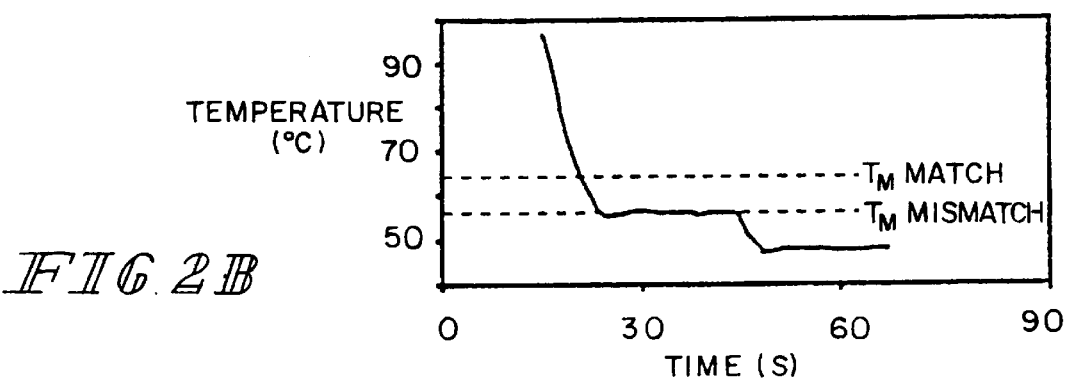
Figure 2C:
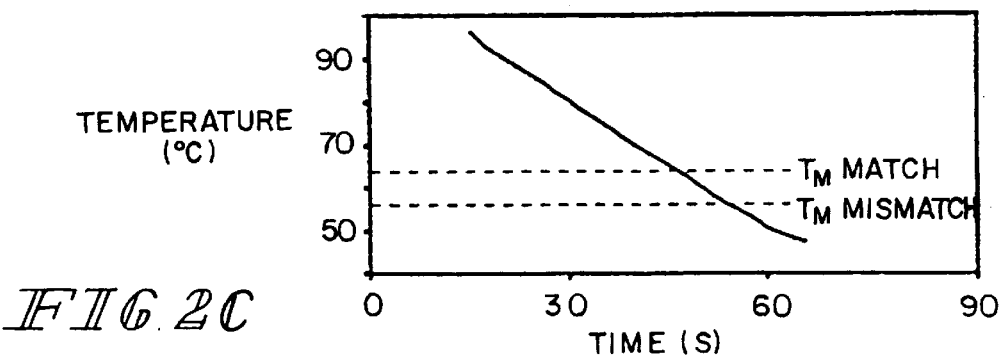
Figure 2D:
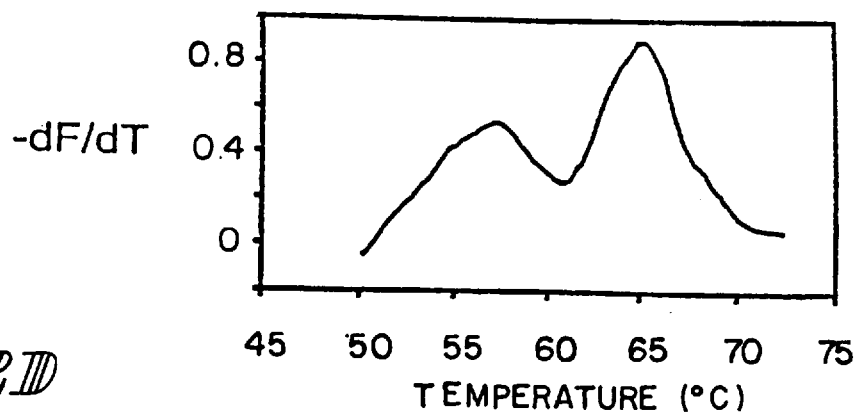
Figure 2E:
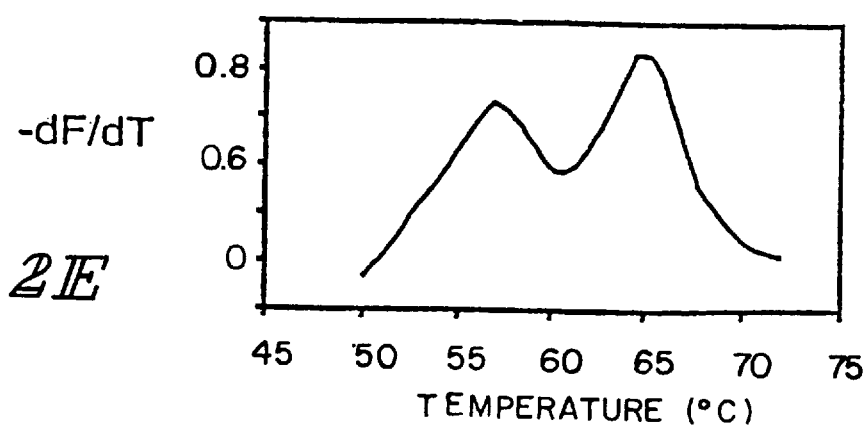
Figure 2F:
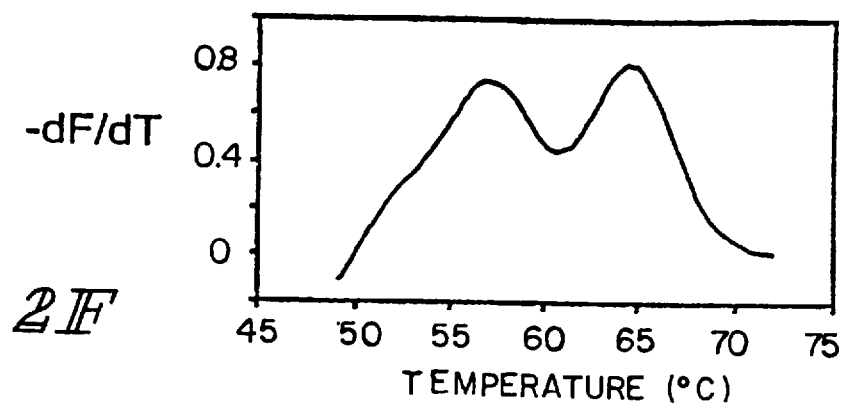

Using target annealing temperatures specific for each site, a gradual transition rate before melting provided the best genotyping (FIG. 2C). In addition, the $MgCl_2$ and target concentrations affect the genotyping quality at each site. A high $MgCl_2$ concentration produces poor peak differentiation for heterozygous genotyping at codon 112, but optimal genotyping at codon 158 in the presence of a low target concentration. Genotyping at codon 158 depends on a low target concentration for better representation of the mismatched duplex. One possible explanation for this is that the higher ratio of probe to target may better insure saturation of both strands of targets prior to melting.

The finding that the sites optimize to different template concentrations suggests that the cycle at which amplification is stopped and investigation of the sequence begins is important. Melting curve analysis usually begins after the plateau phase of amplification is reached. See Bernard, P. S., et al. (1998) Anal. Biochem. 255, 101–107; Bernard, P. S., et al. (1998) Am. J. Pathol. 153, 1055–1061. However, this point may be too late for optimal genotyping at sites such as codon 158. As an alternative, melting curve analysis can be programmed to begin at any cycle to provide optimal genotyping.

A single salt concentration and target concentration was chosen for multiplexing hybridization probes by color. A low salt concentration was chosen due to codon 112 and a low template concentration was chosen due to codon 158. The lower $MgCl_2$ concentration decreased the area of the mismatched peak at codon 158. However, this effect was partly corrected by dropping the annealing temperature for multiplexing farther than 8° C. below the $T_m$, the temperature initially selected. The lower annealing temperature used for multiplexing was not necessary for single-site analysis at codon 158 since equivalent heterozygous peaks could be produced with a higher $MgCl_2$ concentration. In general, it may be necessary to use annealing temperatures lower than 8° C. below the $T_m$ to increase probe/target annealing under low $MgCl_2$ concentrations.

The plateau phase of amplification is to a large extent due to the accumulating complementary product strands competing for primer annealing sites. Wittwer, C. T., et al. (1997) BioTechniques 22, 130–138. This would be consistent with the observed competition during genotyping between the complementary strand and hybridization probes for the target. Although this competition does not prevent melting curve analysis of germ line mutations, it may limit the detection sensitivity of somatic mutations within a background of wild-type product. Various techniques have been developed to circumvent the competition from the nontarget strand during analysis. For example, peptide nucleic acid (PNA) probes effectively compete against the complementary strand by forming an extraordinarily stable duplex with the target. Egholm, M., et al. (1993) Nature 365, 566–568. Another alternative is to bind the target to solid support and then remove the competitor strand. Pastinen, T., et al. (1996) Clin. Chem. 42, 1391–1397. Asymmetric PCR amplification prior to melting curve genotyping would reduce competition while maintaining a homogenous assay. In addition, other techniques directly produce single stranded product, such as nucleic acid sequence-based amplification (NASBA) or rolling-circle amplification. Reitsma, P. H., et al. (1996) Blood Coagul. Fibrinolysis 7, 659–663; Lizardi, P. M., et al.(1998) Nat. Technol. 19, 225–232.

Prior art color compensation algorithms, developed for flow cytometry, do not compensate for changes in signal gains or temperature-dependent crossover effects. The change in crossover coefficients with temperature is not an issue when the temperature remains constant. However, with melting curve analysis, the temperature ranges from 40–95° C. and significant errors arise if the calibration data used to derive the crossover coefficients are obtained at a different temperature than the data to be evaluated. The approach of the present invention is to acquire a calibration run over a slow temperature ramp and to calculate temperature-specific crossover coefficients at each temperature by interpolation of a $3^{rd}$ degree polynomial. That is, a temperature-specific crossover matrix is calculated at the temperature of each data point to be evaluated. Similarly, gain correction is possible by calculating a new matrix from fluorescence values that are multiplied by the gain ratio of the data point to the calibration run. As long as the electronic signal gains are accurate, the new crossover coefficient matrix is matched to the experimental data.

Color compensation for spectral overlap of fluorescent dyes has been modified from flow cytometry techniques. See Bagwell, C. B., and Adams, E. G. (1993) Ann. N.Y. Acad. Sci. 677, 167–184. Custom analysis software was written in LabView (National Instruments, Austin, Tex.). In summary, a calibration run of each pure fluorescent oligonucleotide and autofluorescence control is first obtained with fluorescence values acquired in each channel. Signal crossover constants are calculated from these values and used to convert observed fluorescence (o) to actual signal fluorescence (s) by matrix algebra.

Several modifications to the color compensation algorithms developed for flow cytometry were necessary for use on genotyping data. Following the notation given in Bagwell, C. B., and Adams, E. G. (1993) Ann. N.Y. Acad. Sci. 677, 167–184, hereby incorporated by reference, and eliminating the acquisition of multiple events (relevant to flow cytometry but not to solution fluorescence), the crossover constants are:

$$k(i, j) = \frac{o(i, j) - a(j)}{\sum_{n=1}^{N} [o(i, n) - a(n)]}$$

where:

k(i,j)=crossover signal of dye i in channel j
o(i,j)=observed signal of dye i in channel j
a(j)=autofluorescence in channel j
n=channel index
N=maximum channel Preliminary experiments have shown that the fluorescence of some of the dyes, and the crossover constants of some dye/channel combinations, are temperature dependent over the desired range of analysis (40–95° C). Therefore, calibration runs were obtained by acquiring fluorescence values continuously during a 0.2° C./s temperature ramp from 40 to 95° C. The temperature vs fluorescence curves were nearly linear, but were better approximated by $3^{rd}$ degree polynomials. The $3^{rd}$ degree polynomial coefficients for the temperature vs fluorescence curves of each of the dye/channel combinations and the autofluorescence controls of each channel were stored for temperature interpolation.

To color compensate fluorescence data, the temperature of each acquisition was used to interpolate temperature-specific fluorescence from the calibration curves. These values were then adjusted for any change in electronic gain between the calibration and data run as follows:

$$o(i,j)=[w(i,j)T^3+x(i,j)T^2+y(i,j)T+z(i,j)][G_D(j)/G_C(j)]$$

$$a(j)=[m(j)T^3+n(j)T^2+p(j)T+q(j)][G_D(j)/G_C(j)]$$

where:

w(i,j), x(i,j), y(i,j), and z(i,j) are $3^{rd}$ degree polynomial coefficients for the temperature vs fluorescence curve of dye i in channel j, and m(j), n(j), p(j), and q(j) are $3^{rd}$ degree polynomial coefficients for the temperature vs fluorescence autofluorescence curve in channel j
T=acquisition temperature
$G_D(j)$=gain of channel j during the data run
$G_C(j)$=gain of channel j during the calibration run The actual signal fluorescence of each dye is calculated by the matrix equation:

$$S=K^{-1}[O-A]$$

where:

S=actual signal fluorescence of each dye
K=crossover constant of each dye in each channel
O=observed fluorescence in each channel
A=observed autofluorescence in each channel If temperature correction is desired as well as color compensation, the calibration data are color compensated by the above procedure and the temperature vs actual signal fluorescence curves are fit to $3^{rd}$ degree polynomials and the coefficients stored for temperature interpolation. The data run is color compensated and the fluorescence of each dye during each acquisition is temperature corrected as follows:

$$S_{TC}=S[S_C(T_S)/S_C(T_D)]$$

where:

$S_{TC}$=temperature corrected signal fluorescence
s=signal fluorescence
$S_C(T_S)$=interpolated signal fluorescence from the calibration run at a standard temperature (selected by the user)
$S_C(T_D)$=interpolated signal fluorescence from the calibration run at the data acquisition temperature An example of the results of color compensation and temperature correction is shown in FIGS. 5A–F.

EXAMPLE 1

Preparation of the Oligonucleotides

The human apolipoprotein E gene sequence (GenBank accession K00396) was used to design unlabeled target strands, unlabeled competitor (complementary) strands, and fluorescently labeled probes. The sequences are shown above in Table 1. All oligonucleotides were synthesized by standard phosphoramidite chemistry (Pharmacia Biotech Gene Assembler Plus, Piscataway, N.J). The 5'-labeled LC Red 640 (LightCycler Red 640) and LC Red 705 (LightCycler Red 705) acceptor probes were synthesized using a C6dT amino-modifier (Glen Research, Sterling, Va.) and an LC Red 705 phosphoramidite (Roche Molecular Biochemicals), respectively. The LC Red 640 N-hydroxysuccinimide ester (Roche Molecular Biochemicals) was manually conjugated to an equimolar concentration of oligonucleotide in 0.1 M borate buffer, pH 9.0. Incubation was performed for two hours in the dark. Both acceptor probes were synthesized with a chemical phosphorylation reagent (Glen Research) at the 3' end. The 3'-fluorescein-labeled probes were synthesized on fluorescein-controlled pore glass cassettes (BioGenex, San Ramon, Calif.).

A 5'-trityl group was retained during synthesis on the oligonucleotide target and competitor strands, the pre-conjugated LC Red 640 probe, and the fluorescein-labeled probes. Full-length sequences for all oligonucleotides and probes were purified by reverse-phase C18 high-pressure liquid chromatography (HPLC) using a 3.5$\mu$ Waters Symmetry Column 4.6×150-mm (Waters, Milford, Mass.). The mobile phase consisted of 0.1 mol/L triethylammonium acetate, pH 7.0, and a 10 to 30% (fluorescein probe) or 10 to 80% (unlabeled oligonucleotides and LC Red 705 probe) gradient of acetonitrile (1 ml/minute). The eluate was monitored with tandem absorbance and fluorescence etectors (Waters 486 and 474, Milford, Mass.). For probes, fractions with coincident $A_{260}$ and fluorescence peaks were collected. Final detritylation was performed on a Polypack column (Glen Research, Sterling, Va.) and products were eluted with 50% acetonitrile.

The oligonucleotides and probes were vacuum dried, resuspended in 1 mM Tris-HCl, 0.1 mM EDTA, pH 8.0 and then quantified. Unlabeled oligonucleotides with $A_{260}/A_{280}$ values between 1.6 and 1.8 were used. The concentration ratio of fluorophore to oligonucleotide was calculated for each probe. Probes with ratios outside 0.9 to 1.1 were further purified on a denaturing 15% polyacrylamide gel containing 7 M urea followed by HPLC to remove the urea.

A 3'-fluorescein labeled 17-mer probe was used at each codon for genotyping. Although these probes were different in sequence, both formed an A:C mismatch flanked by C:G pairs when hybridized to the non-complementary target (Table 1). The mismatch in both duplexes was positioned 5 base pairs in from the 3'-end of the probe.

Genotyping at each site was optimized for reagent concentrations and annealing conditions prior to melting curve analysis (see Examples 2 and 3 below). Concentrations of $MgCl_2$, target strand, competitor strand, and fluorescein probe were varied. The $MgCl_2$ concentrations were varied from 1 to 5 mM. The concentrations of target oligonucleotides were varied from 0.05 to 0.2 $\mu M$ and competitor oligonucleotides were at an equimolar concentration to the target strand. Fluorescein-labeled probes were varied from 0.1–0.2 $\mu M$. Each 10 $\mu L$ reaction also contained 50 mM Tris, pH 8.5 (25° C.), 250 $\mu g$/ml bovine serum albumin and 0.2 $\mu M$ of the acceptor probe (LC Red 640 or LC Red 705). FIGS. 2A–C shows the different temperature conditions used for probe annealing prior to genotyping. Heterozygous samples were used to determine optimal conditions for genotyping, assessed as similar shaped Gaussian curves and equivalent peak areas.

A single temperature protocol and common reagents were necessary for multiplex genotyping. The reagents used were 1 mM $MgCl_2$, 0.05 $\mu M$ target oligonucleotides for each site, 0.2 $\mu M$ acceptor probe at each site, 0.1 $\mu M$ fluorescein labeled probe spanning codon 112 and 0.2 $\mu M$ fluorescein labeled probe spanning codon 158. The temperature protocol for multiplex genotyping is given in FIG. 2C.

The samples were loaded into composite plastic/glass capillary cuvettes, capped, briefly centrifuged and loaded into a 32-sample carousel of a thermal cycler with 3-color fluorescence monitoring capability (LightCycler™, Roche Molecular Biochemicals). Twelve samples were included in each melting curve analysis run. During the slow heating (0.1° C./s) phase of the genotyping protocol, fluorescence was continuously monitored with 100 ms acquisitions. The fluorescence values of fluorescein, LC Red 640, and LC Red 705 was acquired in exact temporal coincidence using a linear arrangement of dichroic bandpass filters. See Wittwer, C. T., et al. (1997) BioTechniques 22, 176–181. The data were displayed as fluorescence (F) vs temperature (T) and as derivative fluorescence (-dF/dT) vs temperature plots, as shown in FIGS. 1C and 1D.

EXAMPLE 2

Optimization of Annealing Conditions

The quality of melting curve analysis depends not only on the melting protocol, but also on the annealing conditions before the melting curve acquisition. FIGS. 2A–F show that slow and stepwise temperature annealing protocols result in more symmetrical heterozygous melting peaks then annealing using a single rapid temperature transition. This result was observed even though the total annealing times were approximately the same (compare FIGS. 2A, B, and C), suggesting that linear cooling through the $T_m$s of each duplex favors equal formation of each duplex.

Table 2 shows a comparison of the $T_m$ shifts created by the same mismatch at the two sites using different $MgCl_2$ concentrations. The mismatches destabilize the probe/target duplexes at each site by approximately the same amount. Furthermore, the $\Delta T_m$ between the matched and mismatched duplexes was increased with a higher $MgCl_2$ concentration, while increasing the fluorescein probe concentration increased the $T_m$s of both duplexes without affecting the $\Delta T_m$ (data not shown).

TABLE II

Empirical Melting Temperatures for Fluorescein Probe/Target Duplexes

| [$MgCl_2$] | Codon | Probe: Target Base Pair Genotyping | Duplex $T_m$ | $\Delta T_m$ |
|---|---|---|---|---|
| 1 mM | 112 | A:T | 70.0 | 5.9 |
|  |  | A:C | 64.1 |  |
|  | 158 | A:T | 62.4 | 6.6 |
|  |  | A:C | 55.8 |  |
| 3 mM | 112 | A:T | 71.2 | 6.5 |
|  |  | A:C | 64.7 |  |
|  | 158 | A:T | 64.2 | 7.0 |
|  |  | A:C | 57.2 |  |

Figure 3A:
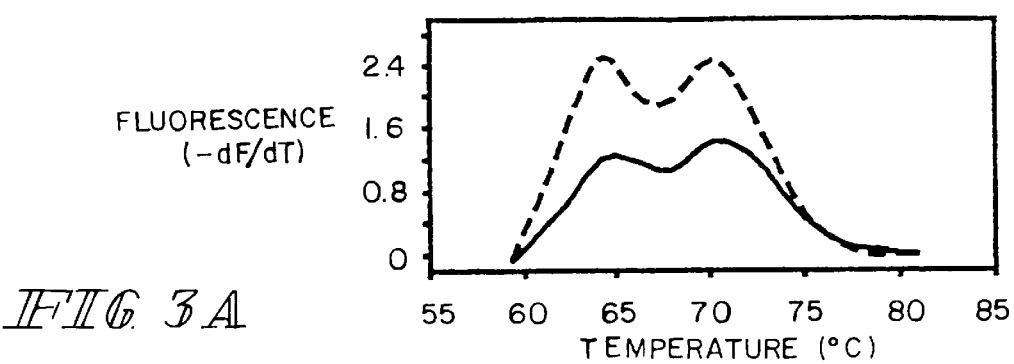
FIGS. 3A–D illustrate the optimization of target oligonucleotide and $Mg^{++}$ concentrations for genotyping codons 112 and 158 of the Apo E gene using the annealing protocol of FIG. 2C.
Figure 3B:
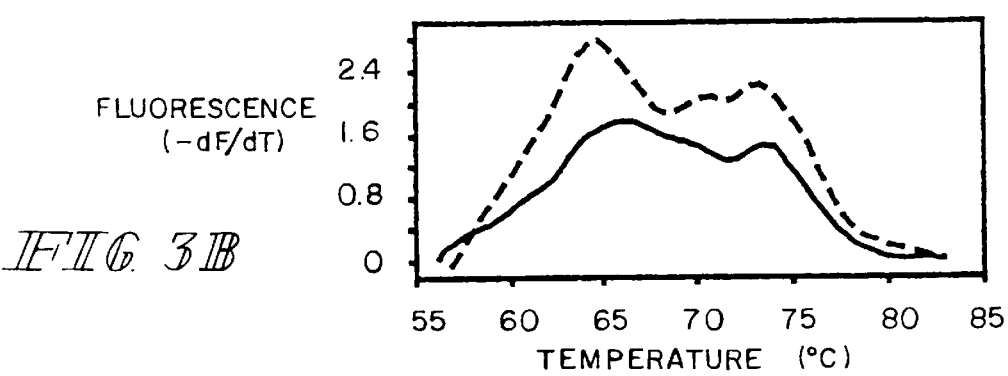
Figure 3C:
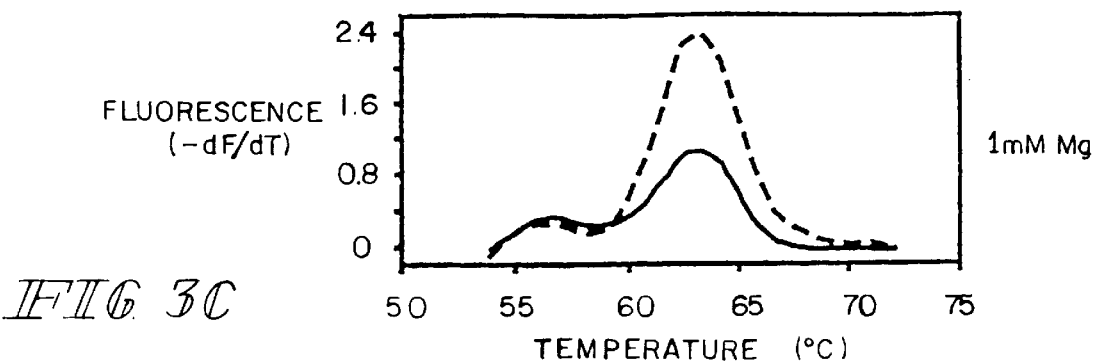
Figure 3D:
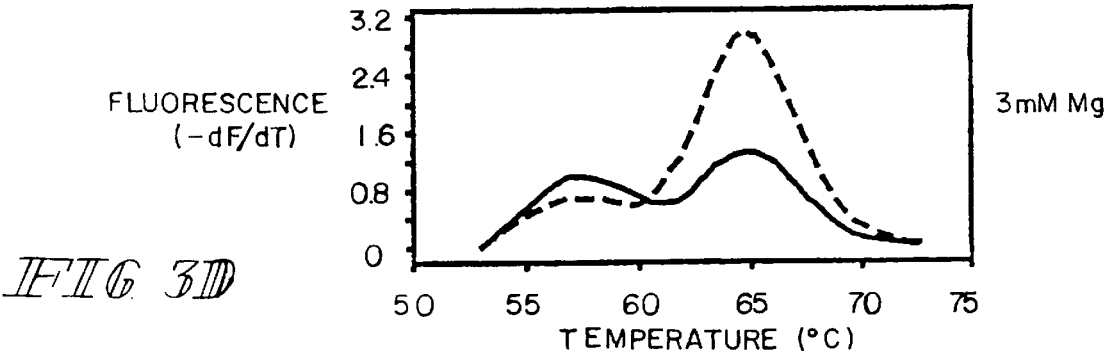

The clear resolution of a heterozygote at codon 112 (spanned by an 82% GC probe) was dependent on a low $MgCl_2$ concentration (FIG. 3A vs 3B). In contrast, heterozygote genotyping at codon 158 (spanned by a 59% GC probe) was more symmetric with a higher $MgCl_2$ concentration and a low target concentration (FIG. 3C vs 3D).

Figure 4A:
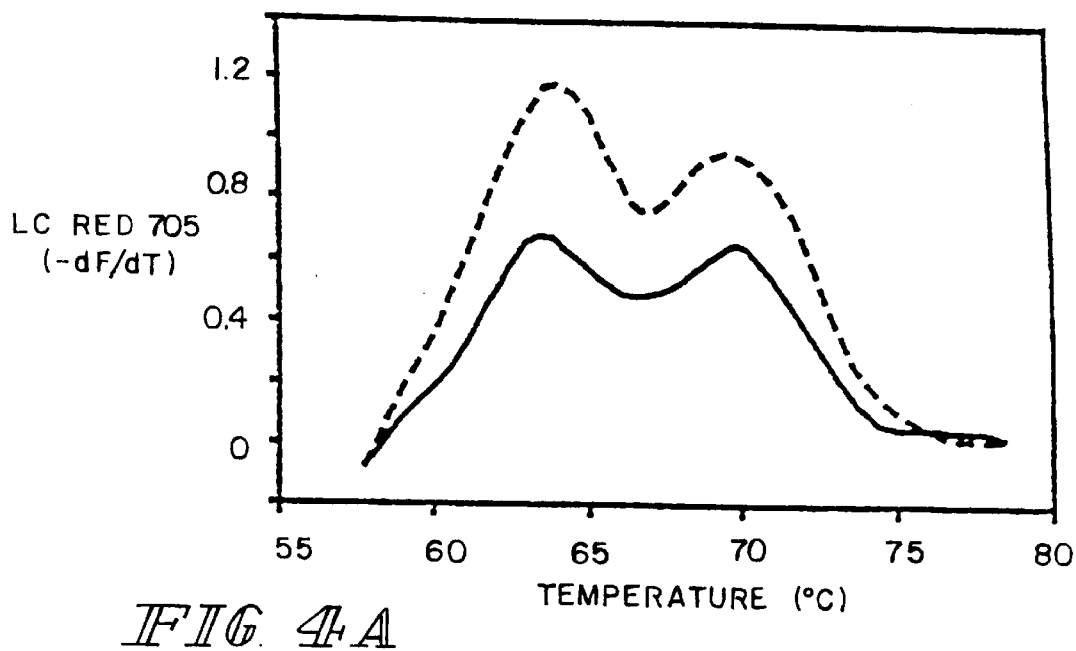
FIGS. 4A–B illustrate competition during genotyping of Apo E targets in the presence of complementary strands, using the annealing protocol of FIG. 2C and plotted as the fluorescence derivative (–dF/dT) vs temperature.
Figure 4B:
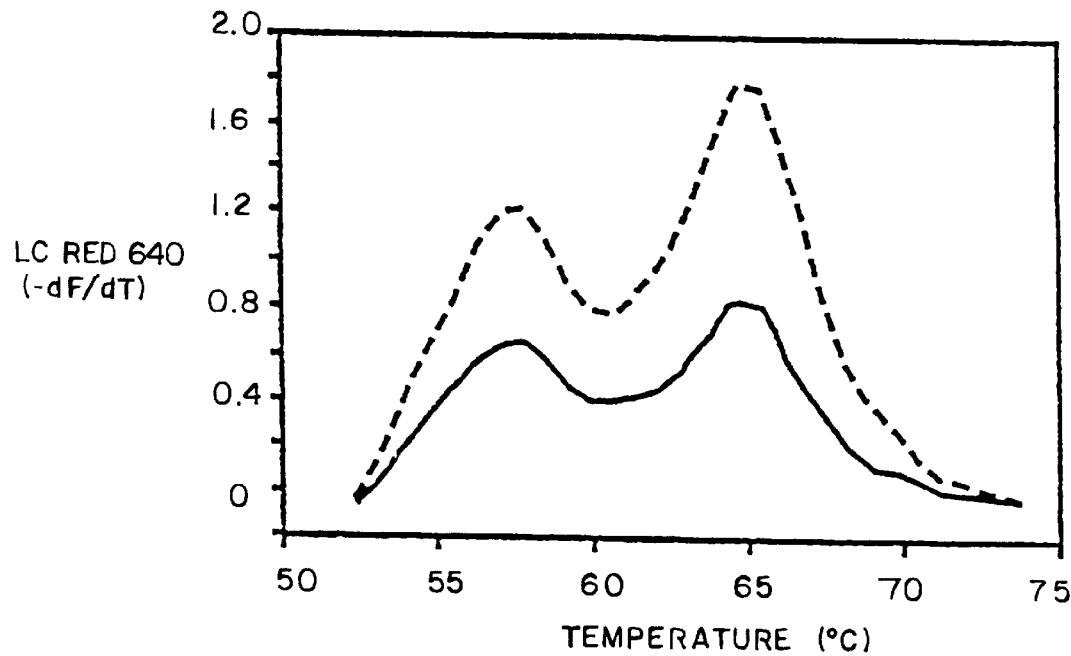

Genotyping from a double stranded product (i.e., equal concentrations of target and complementary strand) is illustrated in FIGS. 4A–B. In the presence of competitor (complementary strand), genotyping optimized to the same parameters shown in FIGS. 3A–D but with a reduction in fluorescence signal to approximately 60 % at each site.

EXAMPLE 3

Color Compensation and Temperature Correction

Figure 5A:
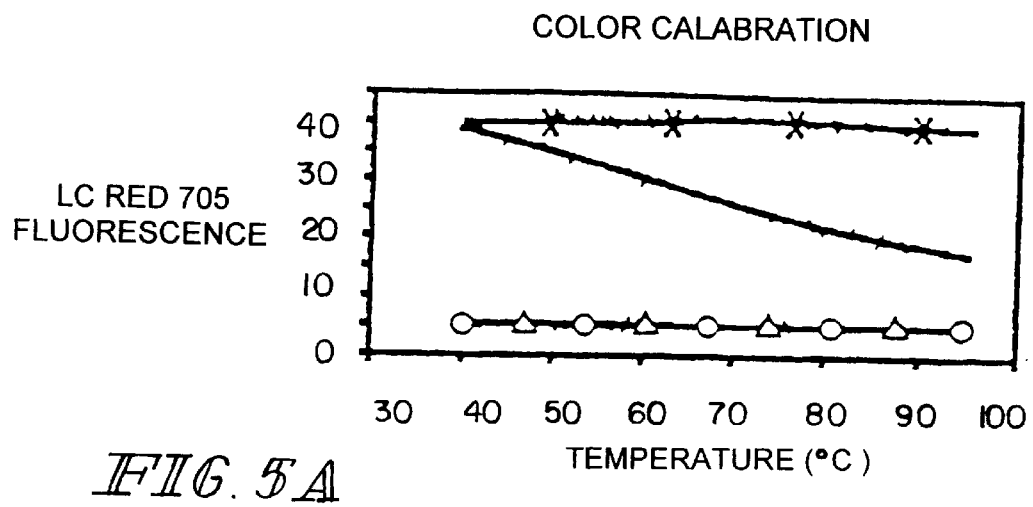
FIGS. 5A–F show calibration and application of color compensation for spectral overlap with compensation of an extreme case of LC Red 640 spillover into the LC Red 705 channel; instrument gains were 1, 30, and 50 for fluorescein, LC Red 640, and LC Red 705 channels respectively; the concentration of labeled probes were 0.1 $\mu$M fluorescein (—o—), 2 $\mu$M LC Red 640 (—X—), and 2 $\mu$M LC Red 705 (—) in 50 mM Tris, pH 8.5 (25° C.), 1 mM $MgCl_2$ and 250 $\mu$M/ml bovine serum albumin, and a sample containing buffer without probes (—$\Delta$—) was included as a blank.
Figure 5B:
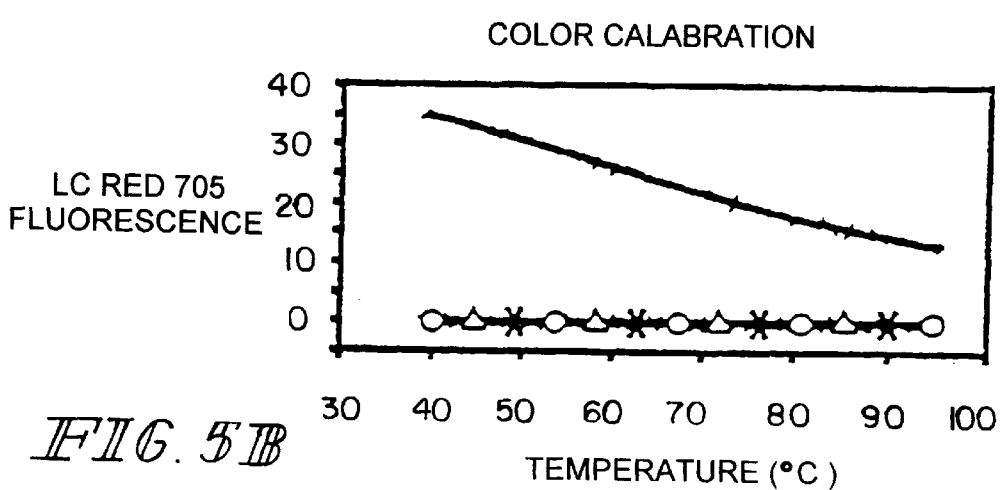
Figure 5C:
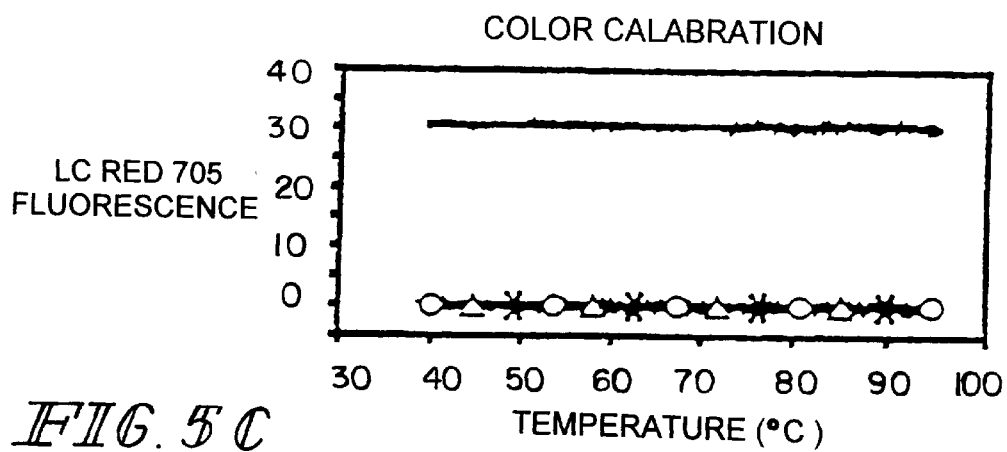
Figure 5D:
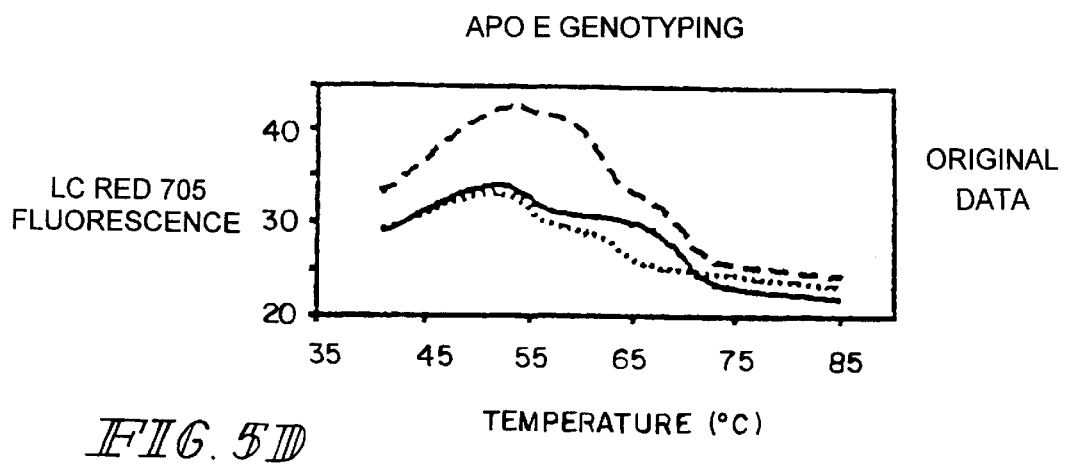
Figure 5E:
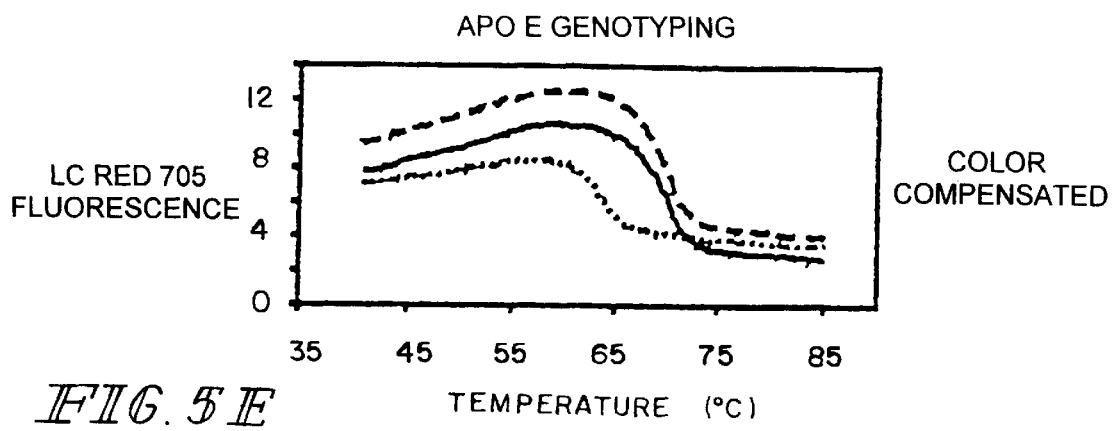
Figure 5F:
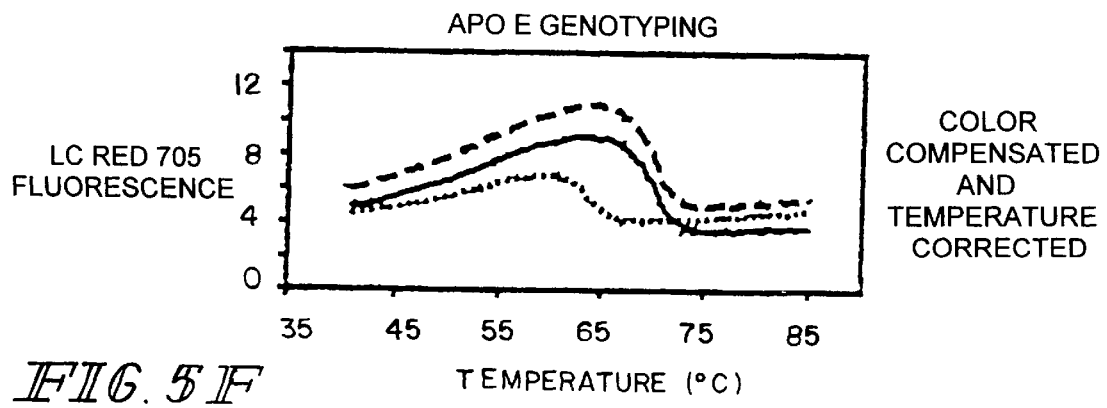

FIGS. 5A–F display the effect of color compensation and temperature correction applied to a calibration run and to color multiplexing of the Apo E locus. The temperature dependence of LC Red 705 is substantial, whereas LC Red 640 fluorescence is almost constant with temperature (FIG. 5A). As expected, only the LC Red 705 calibration sample shows fluorescence after color compensation (FIG. 5B) and the temperature dependence is removed after temperature correction (FIG. 5C). The original fluorescence vs temperature traces for the LC Red 705 channel (codon 112) are complex and not interpretable because of fluorescence overlap from LC Red 640 (FIG. 5D). However, single temperature transitions are discerned after color compensation (FIG. 5E). After temperature correction (FIG. 5F), the baseline slope outside of the melting transition region is increased.

Figure 6A:
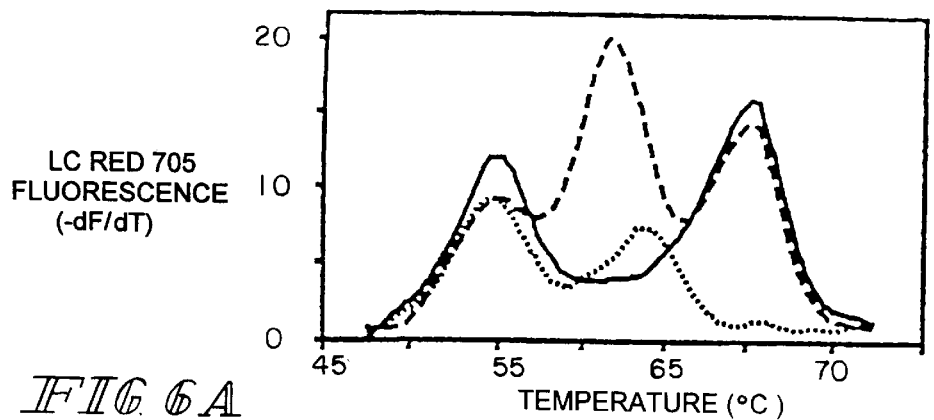
Figure 6B:
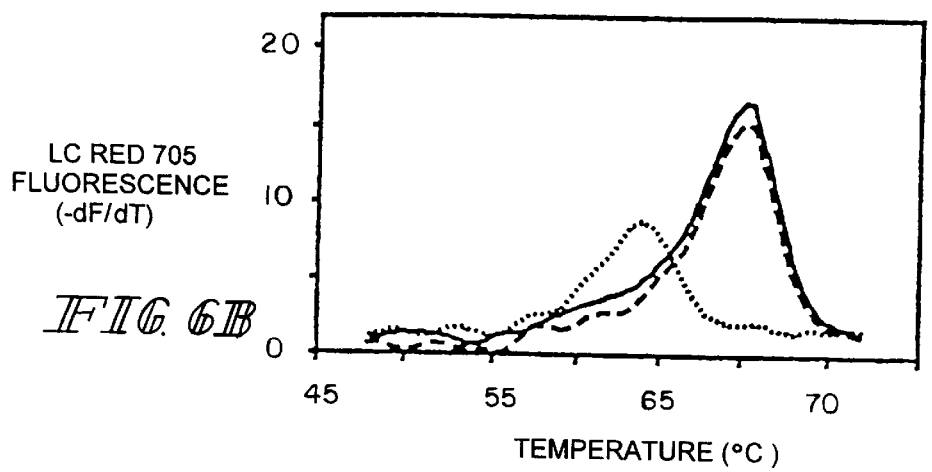

Multiplexing by color and $T_m$ provides simultaneous identification of variants at codons 112 and 158 in a single tube within 10 minutes. FIGS. 6A–B show the uncompensated (A) and compensated (B) fluorescent melting peaks for genotyping codon 112. Without compensation, there is substantial bleed over from the LC Red 640 acceptor dye into the channel for monitoring the LC Red 705 acceptor dye (FIG. 6A). This results in apparent products with $T_m$s of 55° C. and 62° C. However these additional peaks disappear after compensation, revealing the true homozygous genotypes at codon 112. All the genotypes for the 6 naturally occurring Apo E protein isoforms could be distinguished using this method. In addition, the other 3 possible genotypes not normally found in human populations were constructed using synthesized templates and were correctly analyzed (data not shown).

Figure 7A:
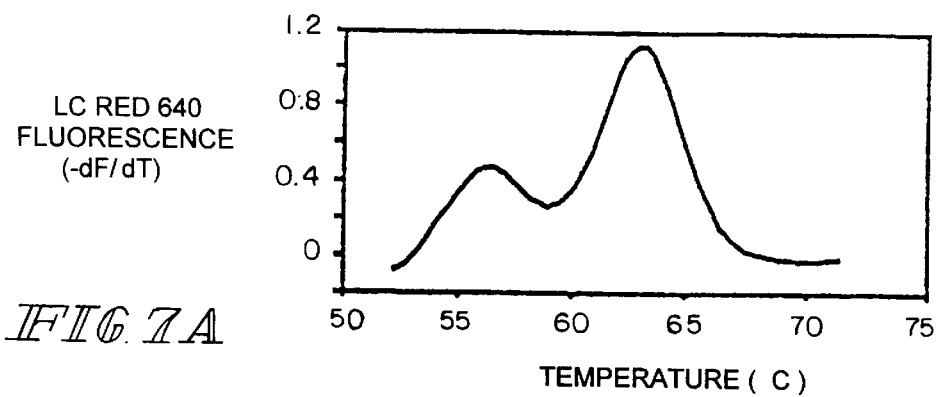
FIGS. 7A–B show the effect of a lower annealing temperature on peak area for the mismatched $\epsilon3$ in genotyping of the heterozygous $\epsilon2/\epsilon3$ sample.
Figure 7B:
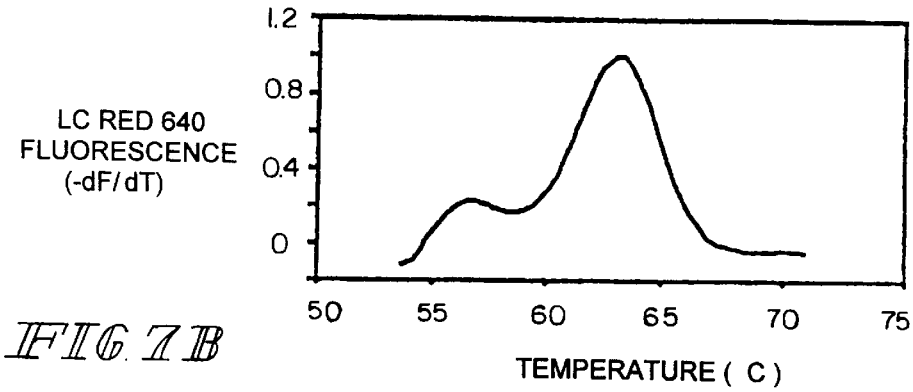

Multiplex genotyping was optimal using low concentrations of both target and $MgCl_2$. Using the lower $MgCl_2$ concentration for genotyping codon 158 decreased the peak area of the mismatched duplex. Nevertheless, this resulting asymmetry in the heterozygous peaks could be partially compensated for by lowering the annealing target temperature (from 48° C. to 42° C.) before melting (FIGS. 7A–B).

Although the invention has been described in detail with reference to preferred embodiments, variations and modifications exist within the scope and spirit of the invention as described and defined in the following claims.

What is claimed is:

1. A method for determining the presence of at least two analytes in a sample, comprising:
providing at least two detecting entities, each of said entities comprising a fluorescent label different from the fluorescent label of any of the other detecting entities, and each of said entities capable of specific binding with their respective analytes,
contacting the sample with the detecting entities to allow specific binding of the analytes and detecting entities,
exciting each of said labels with light having an appropriate wavelength for inducing fluorescence,
determining values of fluorescence of the labels in at least two different spectral channels, and
compensating said values for spectral overlap, wherein the compensating step includes correcting for temperature dependence of the fluorescent values.

2. The method of claim 1 wherein the determining step is performed throughout a range of temperatures.

3. The method of claim 2 wherein the correction for temperature dependence is performed through calculating a temperature specific overlap coefficient.

4. The method of claim 1 wherein the analytes are nucleic acid amplification products.

5. The method of claim 4 further comprising the step of determining the genotype of each of the nucleic acid amplification products.

6. The method of claim 1 further comprising the step of compensating said values for amplifier gain.

7. A method of analyzing the genotype of multiple loci of nucleic acid sequences comprising the steps of:
providing a sample of nucleic acid having a first locus and a second locus,
providing a first detecting entity, the first detecting entity comprising a first fluorescent label and having specificity for the first locus,
providing a second detecting entity, the second detecting entity comprising a second fluorescent label and having specificity for the second locus,
contacting the sample of nucleic acid with the first and second detecting entities,
exciting the first and second entities with light having the appropriate wavelength to induce fluorescence of the first and second fluorescent labels,
measuring throughout a range of temperatures a first fluorescent signal of the first detecting entity in a first spectral channel and a second fluorescent signal of the second detecting entity in a second spectral channel, and
compensating the first and second signal values for temperature dependence of the fluorescent signals.

8. The method of claim 7 wherein the compensating step is performed through calculating a temperature dependent coefficient.

9. The method of claim 8 further comprising the step of compensating for amplifier gain.

10. The method of claim 7 wherein the first detecting entity further comprises a sequence of nucleic acid complementary to at least a portion of the first locus and the second detecting entity further comprises a sequence of nucleic acid complementary to at least a portion of the second locus.

11. The method of claim 10 wherein the contacting step includes annealing the first and second detecting entities to their respective loci, and the measuring step includes monitoring fluorescent signals in the spectral channels during heating to melt the detecting entities from their respective loci.

12. The method of claim 11 wherein the contacting step is performed by lowering the temperature by 1° C./s.

13. The method of claim 7 wherein the first fluorescent label comprises a first donor dye, a first acceptor dye, and a first pair of oligonucleotides, each oligonucleotide attached to one of the dyes, and each oligonucleotide substantially complementary to neighboring regions of the first locus.

14. The method of claim 13 wherein the second fluorescent label comprises a second donor dye, a second acceptor dye, and a second pair of oligonucleotides, each oligonucleotide attached to one of the dyes, and each oligonucleotide substantially complementary to neighboring regions of the second locus.

15. The method of claim 14 wherein the first donor dye is fluorescein and the first acceptor dye is LC Red 705.

16. The method of claim 15 wherein the second donor dye is fluorescein and the second acceptor dye is LC Red 640.

17. The method of claim 13 wherein the first locus has multiple alleles and the $Mg^{++}$ concentration is optimized to produce relatively even melting peaks for the alleles when the compensated signal values are plotted as $-dF/dT$ vs temperature.

18. The method of claim 13 wherein the first locus has multiple alleles and the concentration of the nucleic acid comprising the first locus is optimized to produce relatively even melting peaks for the alleles when the compensated signal values are plotted as $-dF/dT$ vs temperature.

* * * * *